United States Patent
Yoon et al.

(10) Patent No.: US 11,574,726 B2
(45) Date of Patent: Feb. 7, 2023

(54) IMAGE ANALYSIS METHOD FOR MULTICENTER STUDY AND SYSTEM THEREOF

(71) Applicant: Wonkwang University Center for Industry-Academy Cooperation, Jeollabuk-do (KR)

(72) Inventors: Kwon Ha Yoon, Jeollabuk-do (KR); Seung Jin Kim, Jeollanam-do (KR); Ji Eon Kim, Jeju-do (KR); Si Hyung No, Jeollabuk-do (KR); Tae Hoon Kim, Jeollabuk-do (KR); Chang Won Jeong, Jeollabuk-do (KR)

(73) Assignee: Wonkwang University Center for Industry-Academy Cooperation, Jeollabuk-Do (KR)

( * ) Notice: Subject to any disclaimer, the term of this patent is extended or adjusted under 35 U.S.C. 154(b) by 745 days.

(21) Appl. No.: 16/527,678

(22) Filed: Jul. 31, 2019

(65) Prior Publication Data

US 2020/0043599 A1     Feb. 6, 2020

(30) Foreign Application Priority Data

Aug. 1, 2018    (KR) .................. 10-2018-0089747

(51) Int. Cl.
*G16H 80/00*    (2018.01)
*G16H 30/20*    (2018.01)
(Continued)

(52) U.S. Cl.
CPC ............ *G16H 30/20* (2018.01); *G16H 10/20* (2018.01); *G16H 70/00* (2018.01); *G16H 80/00* (2018.01)

(58) Field of Classification Search
CPC ........ G16H 30/20; G16H 10/20; G16H 70/00; G16H 80/00; G16H 30/40; G16H 50/70
See application file for complete search history.

(56) References Cited

U.S. PATENT DOCUMENTS

2004/0122702 A1*    6/2004    Sabol .................... G06Q 10/10
                                                                706/45
2004/0122703 A1*    6/2004    Walker .................. G16H 50/70
                                                                706/45

(Continued)

FOREIGN PATENT DOCUMENTS

JP    2007-140647 A    6/2007
KR    10-2011-0066576 A    6/2011
KR    10-2013-0099320 A    9/2013

OTHER PUBLICATIONS

Office action dated Feb. 20, 2020 from Korean Patent Office in a counterpart Korean Patent Application No. 10-2018-0089747 (all the cited references are listed in this IDS.) (English translation is also submitted herewith.).

*Primary Examiner* — Hien L Duong
(74) *Attorney, Agent, or Firm* — The PL Law Group. PLLC

(57) ABSTRACT

An image analysis method for multicenter study includes, by a multicenter study support system, recruiting and selecting a plurality of agency systems to perform multicenter study, and then distributing an analysis guide and an analysis program corresponding to a purpose and condition of the multicenter study to each of the agency systems, by each of the agency systems, collecting analysis data acquired through the analysis guide and the analysis program and then uploading the analysis data to the multicenter study support system, and by the multicenter study support system, collecting and processing the uploaded analysis data, and then sharing the data processing result with each of the agency systems.

8 Claims, 6 Drawing Sheets

(51) Int. Cl.
*G16H 70/00* (2018.01)
*G16H 10/20* (2018.01)

(56) References Cited

U.S. PATENT DOCUMENTS

| | | | |
|---|---|---|---|
| 2004/0122704 A1* | 6/2004 | Sabol | G07C 9/37 |
| | | | 706/45 |
| 2008/0256128 A1* | 10/2008 | Pierce | G16H 15/00 |
| 2013/0231943 A1* | 9/2013 | Fueki | G06Q 10/10 |
| | | | 705/2 |
| 2016/0140305 A1* | 5/2016 | Takeyama | G16Z 99/00 |
| | | | 705/3 |
| 2019/0287686 A1* | 9/2019 | Takeda | G16H 80/00 |

* cited by examiner (a)         (b)         (c)

IMAGE ANALYSIS METHOD FOR MULTICENTER STUDY AND SYSTEM THEREOF

CROSS-REFERENCE TO RELATED APPLICATION AND CLAIM OF PRIORITY

This application claims priority to Korean Patent Application No. 10-2018-0089747 filed on Aug. 1, 2018 in the Korean Intellectual Property Office (KIPO), the entire disclosure of which is incorporated by reference herein.

This study was supported by the grants of the National Research Foundation of Korea (NRF) (2016M3A9A7918501) and the Korea Health Technology R&D Project through the Korea Health Industry Development Institute (KHIDI), funded by the Ministry of Health & Welfare (HI18C1216).

BACKGROUND

1 Technical Field

This disclosure relates to an image analysis method and system for multicenter study, and more particularly, to a method and system for multicenter image analysis study, which allows a plurality of agencies participating in the multicenter study to acquire, analyze and share an image for multicenter study under the same analysis environment.

2. BACKGROUND ART

Multicenter study is a research in which a plurality of agencies performs the same clinical and preclinical studies together. Recently, the multicenter study is gradually increasing since it is able to derive higher quality research results while reducing study time compared to single studies. Also, the value of standardized data is becoming important.

However, in the multicenter study, it is demanded to manage standardized forms for quality research, but research agencies use different data collection and analysis methods.

Thus, it is difficult to integrally manage the data acquired by different research agencies, which frequently reduces the efficiency of the multicenter study.

In particular, it is practically impossible to carry out the multicenter study based on image. Since image is just information in itself and is not a numerical value, it is very difficult to determine which image is to be selected and shared for the multicenter study.

SUMMARY

This disclosure is to solve the above problems, and the present disclosure is directed to providing an image analysis method and system for multicenter study, which enables a plurality of agencies participating in the multicenter study to acquire analysis data under the same analysis environment, so that the plurality of agencies are able to perform integrated research through the analysis based on software that is to be developed based on a standardization protocol.

In addition, the present disclosure is directed to providing an image analysis method and system for multicenter study, which allows a plurality of agencies to analyze patient images and then selectively sharing the patient images based on the analysis results, so that the multicenter study method may also be smoothly performed based on image.

The objects of the present disclosure are not limited to the above, and other objects not mentioned herein may be clearly understood by those skilled in the art from the following description.

In one general aspect, there is provided a multicenter study support system, comprising: a manifold recruiting unit configured to recruit and select a plurality of research agencies to perform multicenter study; an analysis environment synchronizing unit configured to acquire an analysis guide and an analysis program corresponding to a purpose and condition of the multicenter study and distribute to each of the research agencies; an analysis data collecting unit configured to collect and store analysis data acquired by each of the research agencies through the analysis guide and the analysis program; and an analysis data processing unit configured to process the collected analysis data in a preset manner and share the data processing result with each of the research agencies.

The analysis program may be a program for selecting and processing a medical image, then generating analysis data containing at least one of the selected image, the image processing result and an image conversion result, and uploading the analysis data to the multicenter study support system, and the analysis guide may be information in which at least one of a data collection amount, a research period, a research target selecting condition, an analyzing image selecting condition, a research exclusion condition, an analysis program kind and an analysis program execution environment is predefined.

The medical image may be at least one of a CT (computerized tomography) image, a MRI (magnetic resonance imaging) image and an ultrasonic image, which is stored in the form of a DICOM (digital imaging and communication in medicine) file.

At this time, the analysis program may further have a function of anonymizing a DICOM header and patient information mapped with the medical image.

In another aspect of the present disclosure, there is also provided an agency system, comprising: an analysis environment building unit configured to receive and install an analysis guide and an analysis program provided from a multicenter study support system and adjust a program execution period, an image selecting condition and an analysis program execution environment according to the analysis guide; a patient database configured to store and manage medical treatment information of a plurality of patients and provide the medical treatment information to the analysis program; and an analysis control unit configured to select at least one medical image by searching the patient database according to the image selecting condition, then analyze the medical image through the analysis program to obtain analysis data, and upload the analysis data to the multicenter study support system.

The analysis guide may be information in which at least one of a data collection amount, a research period, a research target selecting condition, an analyzing image selecting condition, a research exclusion condition, an analysis program kind and an analysis program execution environment is predefined.

The medical image may be at least one of a CT image, an MRI image and an ultrasonic image, which is stored in the form of a DICOM file.

In addition, the analysis control unit may further have a function of anonymizing a DICOM header and patient information mapped with the medical image.

In another aspect of the present disclosure, there is also provided an image analysis method for multicenter study, comprising: by a multicenter study support system, recruiting and selecting a plurality of agency systems to perform multicenter study, and then distributing an analysis guide and an analysis program corresponding to a purpose and condition of the multicenter study to each of the agency systems; by each of the agency systems, collecting analysis data acquired through the analysis guide and the analysis program and then uploading the analysis data to the multicenter study support system; and by the multicenter study support system, collecting and processing the uploaded analysis data, and then sharing the data processing result with each of the agency systems.

Since a plurality of agencies participating in the manifest research of the present disclosure is able to acquire analysis data under the same analysis environment, it is possible to integrally manage and process analysis data for the multicenter study more efficiently. In particular, by using a shared image analysis system, it is possible to collect, analyze and integrate consistent images based on a standardized protocol, which may lead to a medical image big data research.

In addition, since a plurality of agencies individually analyze patient images and then selectively share the patient images based on the analysis result, it is possible to perform image-based multicenter study.

DETAILED DESCRIPTION

The objects and effects of the present disclosure and the technical features for achieving them will become apparent with reference to the embodiments described in detail below along with the accompanying drawings. In the following description of the present disclosure, known functions or configurations will not be described in detail when it is determined that the gist of the present disclosure may be unnecessarily obscured thereby.

In addition, the following terms are defined in consideration of the functions in the present disclosure and may vary depending on the intention of a user or an operator, or the customs.

However, the present disclosure is not limited to the embodiments disclosed below, but may be implemented in various other ways. The embodiments are provided just for perfect explanation of the present disclosure and for allowing those of skilled in the art to completely understand the present disclosure, and the present disclosure is defined only by the scope of the claims. Therefore, the definition should be based on the contents throughout the specification.

Figure 1:
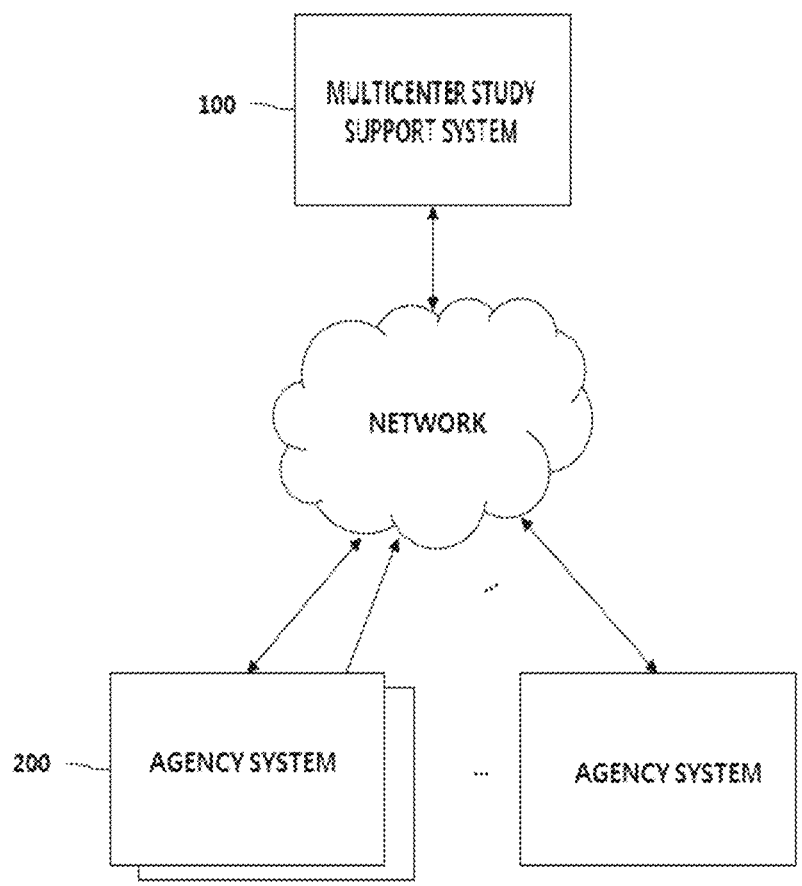
FIG. 1 is a diagram showing an image analysis system for multicenter study according to an embodiment of the present disclosure.

FIG. 1 is a diagram showing an image analysis system for multicenter study according to an embodiment of the present disclosure.

Referring to FIG. 1, the image analysis system for multicenter study according to the present disclosure includes a multicenter study support system 100 and a plurality of agency systems 200. The multicenter study support system 100 allows the plurality of agency systems 200 participating in the same research to analyze images under the same analysis environment, and also collects and integrally processes image analysis results of each of the plurality of agency systems 200 such that the image analysis results are shared by the plurality of agency systems 200.

Figure 2:
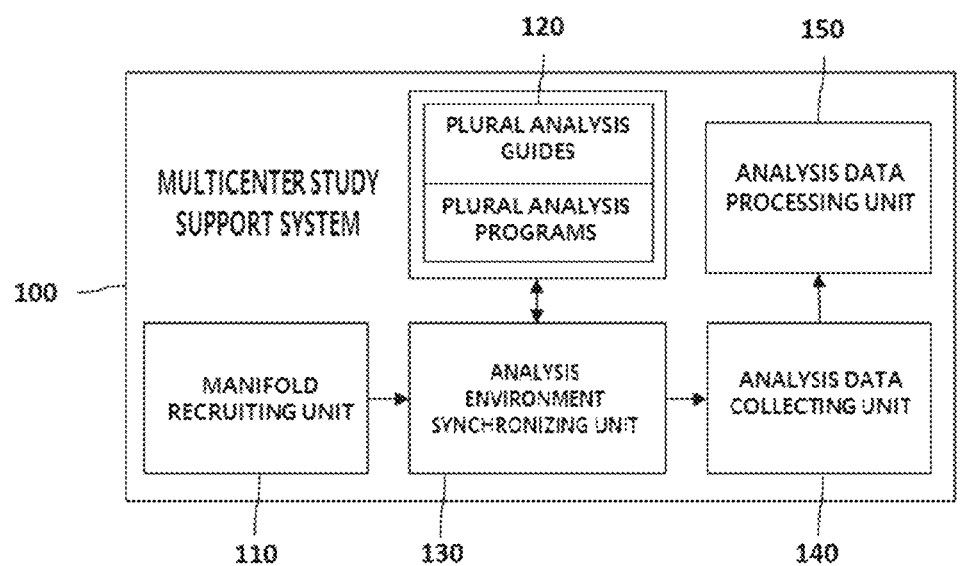
FIG. 2 is a diagram showing a multicenter study support system according to an embodiment of the present disclosure.

FIG. 2 is a diagram showing a multicenter study support system according to an embodiment of the present disclosure.

Referring to FIG. 2, the manifest research support system 100 of the present disclosure may include a manifold recruiting unit 110, a database (DB) 120, an analysis environment synchronizing unit 130, an analysis data collecting unit 140, and an analysis data processing unit 150.

If it is approved to perform the multicenter study, the manifold recruiting unit 110 generates and distributes a recruitment message to recruit agencies to participate in the multicenter study. In addition, the manifold recruiting unit 110 evaluates a plurality of applications received in response to the advertisement message and selects a plurality of agencies to conduct the multicenter study.

The DB 120 stores and manages a plurality of analysis guides and analysis programs, respectively corresponding to the purpose (for example, cancer drug development, diabetes treatment, and so on) and conditions (for example, a data collection amount, a research period, a research target selecting condition, an analyzing image selecting condition, a research exclusion condition, and so on) of the multicenter study.

At this time, the analysis program is a program for performing image processing on at least one of a CT image, an MRI image and an ultrasonic image, and may include various image processing functions such as a ROI (Region Of Interest) extraction function, an analysis value measurement function, an image conversion function, a disease diagnosis function, and so on. The analysis guide may be information in which a data collection amount, a research period, a research target selecting condition, an analyzing image selecting condition, a research exclusion condition, an analysis program kind and an analysis program execution environment are predefined.

The analysis environment synchronizing unit 130 searches the DB 120 and obtains an analysis guide and an analysis program corresponding to the purpose and condition of the multicenter study that is to be performed at present, and transmits the analysis guide and the analysis program to the plurality of agency systems 200 respectively corresponding to the agencies selected by the manifold recruiting unit 110.

The analysis data collecting unit 140 collects and stores all the analysis data obtained through the analysis guide and the analysis program provided by the analysis environment synchronizing unit 130 by each of the plurality of agency systems 200.

The analysis data processing unit 150 performs statistical processing on the analysis data collected and stored by the analysis data collecting unit 140, and shares statistical processing results with the plurality of agency systems 200. For example, the analysis data processing unit 150 classifies and collects the analysis data based on at least one of a treatment period, a treatment condition, a sex and a region, and then calculates and provides the statistics for the analysis data. In addition, the analysis data processing unit 150 generates and provides an analysis data search menu and allows each of the plurality of agency systems 200 to search and download required analysis data.

Figure 3:
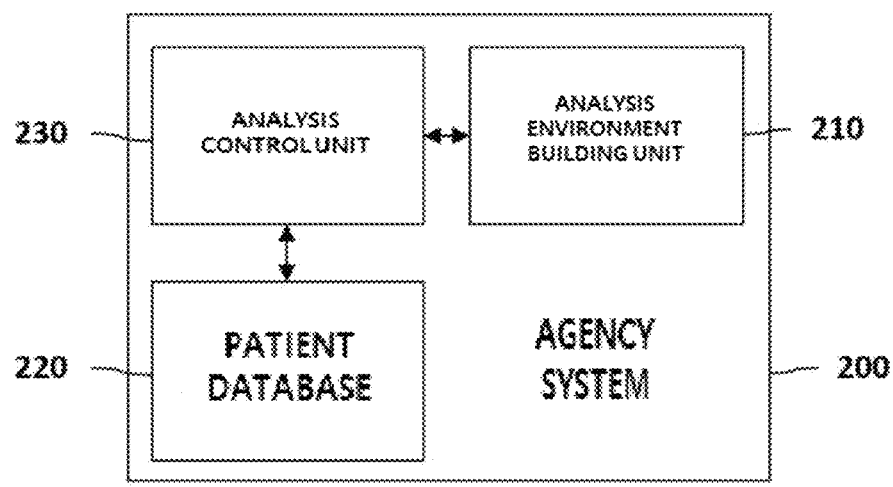
FIG. 3 is a diagram showing an agency system according to an embodiment of the present disclosure.

FIG. 3 is a diagram showing an agency system according to an embodiment of the present disclosure.

Referring to FIG. 3, the agency system 200 of the present disclosure may include an analysis environment building unit 210, a patient database 220, and an analysis control unit 230.

The analysis environment building unit 210 stores and installs the analysis guide and the analysis program transmitted from the multicenter study support system 100, and then adjusts the program execution period, the image selecting condition and the analysis program execution environment according to the analysis guide. That is, the analysis environment building unit 210 allows all the agency systems performing the same research under the control of the multicenter study support system 100 to establish the same analysis environment.

The patient database 220 stores and manages medical treatment information of a plurality of patients. In particular, the patient medical treatment information may include a medical image obtained by photographing a specific body region of the patient in addition to patient personal information and a medical chart. At this time, the medical image may be at least one of a CT image, an MRI image and an ultrasonic image.

The analysis control unit 230 determines whether or not to execute the analysis program by referring to the research period of the analysis guide stored in the analysis environment building unit 210 and selects patient images to be analyzed through the analysis program according to the research target selecting condition and the analyzing image selecting condition. After the analysis data is obtained by analyzing the patient images selected through the analysis program, the analysis data is uploaded to the multicenter study support system 100.

At this time, the analysis data may be the image analysis result itself, the image analysis result may be an image overlaid on the original image, or the image analysis result and the patient image may be separately provided information.

Figure 4:
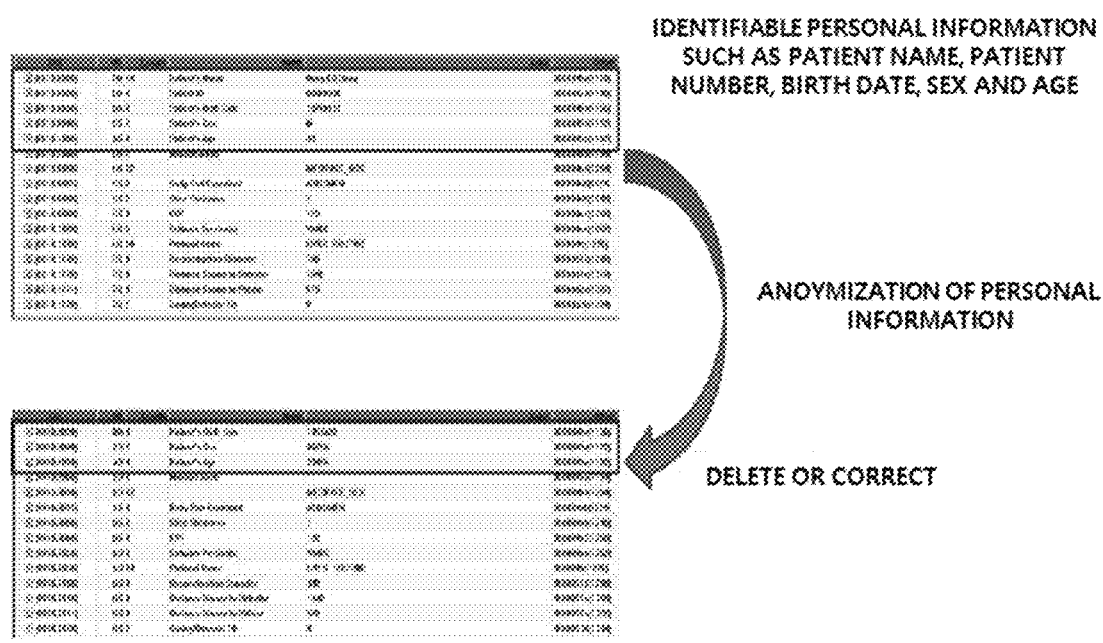
FIGS. 4 and 5 are diagrams for illustrating an image analysis method for multicenter study according to an embodiment of the present disclosure.
Figure 5:
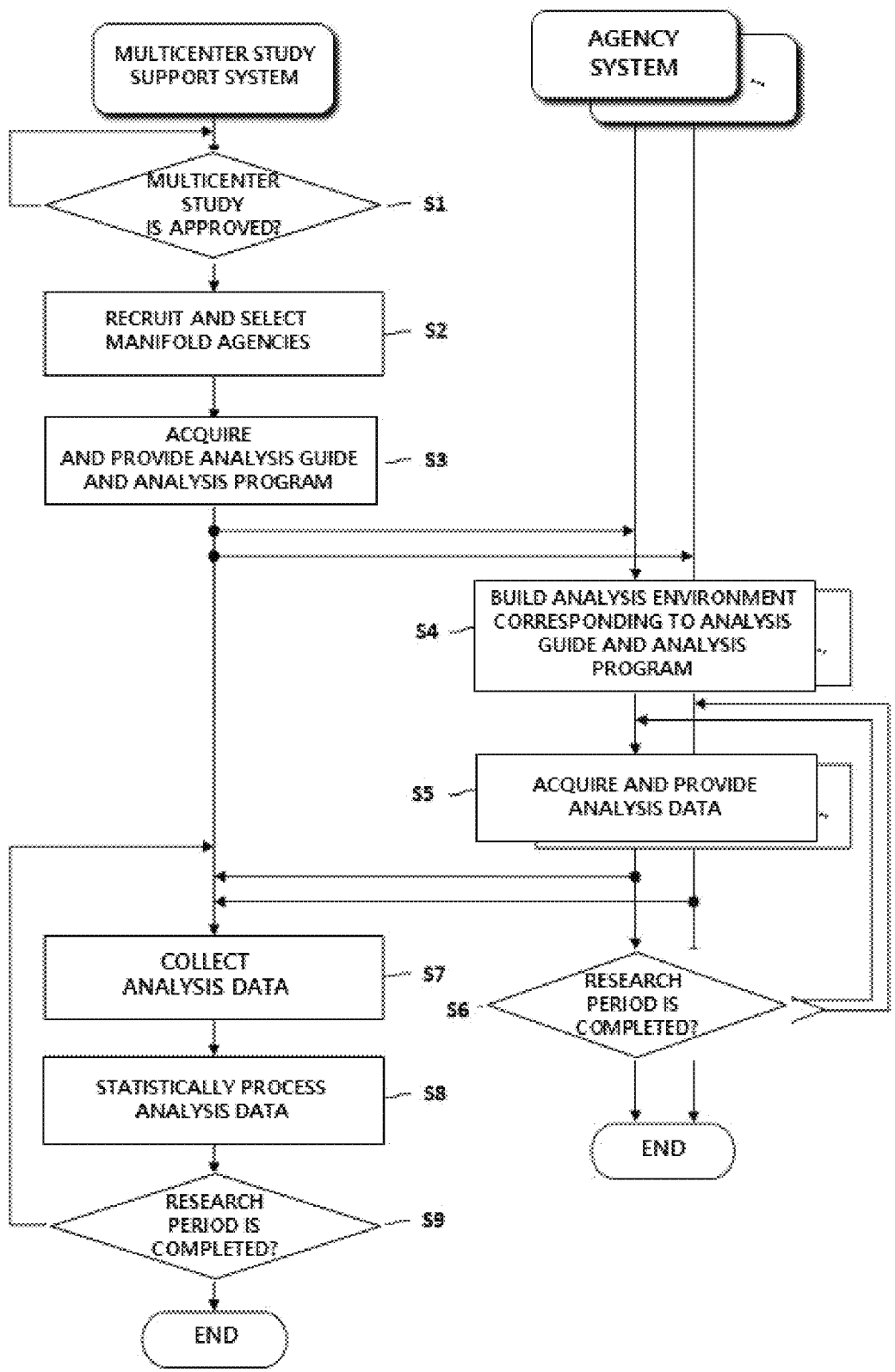

In addition, the analysis control unit 230 further includes a function of anonymizing the patient information mapped with the original image, thereby preventing the patient information from being exposed and misused by a third party. For example, most medical images are standardized in the form of a DICOM file, and the DICOM file includes an original image and tag information. In addition, the tag information mapped with the original image contains a name, a patient number, an age, sex, and so on corresponding to the patient personal information. Thus, in the present disclosure, the medical image is completely anonymized by anonymizing a DICOM header and simultaneously deleting or correcting some of the personal-identifiable information included in the tag information as shown in FIG. 4 (namely, by anonymizing the patient information mapped with the original image).

FIGS. 5 to 8 are diagrams for illustrating an image analysis method for multicenter study according to an embodiment of the present disclosure.

If the multicenter study requested by a medical agency or pharmaceutical company is approved (S1), the multicenter study support system 100 provides the purpose and condition of the multicenter study described in an institutional review board (IRB) application submitted by the medical agency or the pharmaceutical company, and also generates a recruitment message for recruiting agencies to participate in the multicenter study and distributes the recruitment message to various medical agencies. In addition, the multicenter study support system 100 evaluates all application forms submitted in response to the recruitment message, and then selects a plurality of agencies to conduct the multicenter study based on evaluation scores (S2).

In addition, the multicenter study support system 100 acquires an analysis guide and an analysis program that satisfies the purpose and condition of the multicenter study, and then provides the analysis guide and the analysis program to each of the plurality of agency systems 200 respectively corresponding to the agencies selected in Step S2 (S3).

Then, each of the plurality of agency systems 200 determines the program execution period, the image selecting condition, and so on according to the analysis guide, and adjusts the analysis program execution environment such that all the plurality of agency systems 200 have the same analysis environment (S4).

Figure 6:
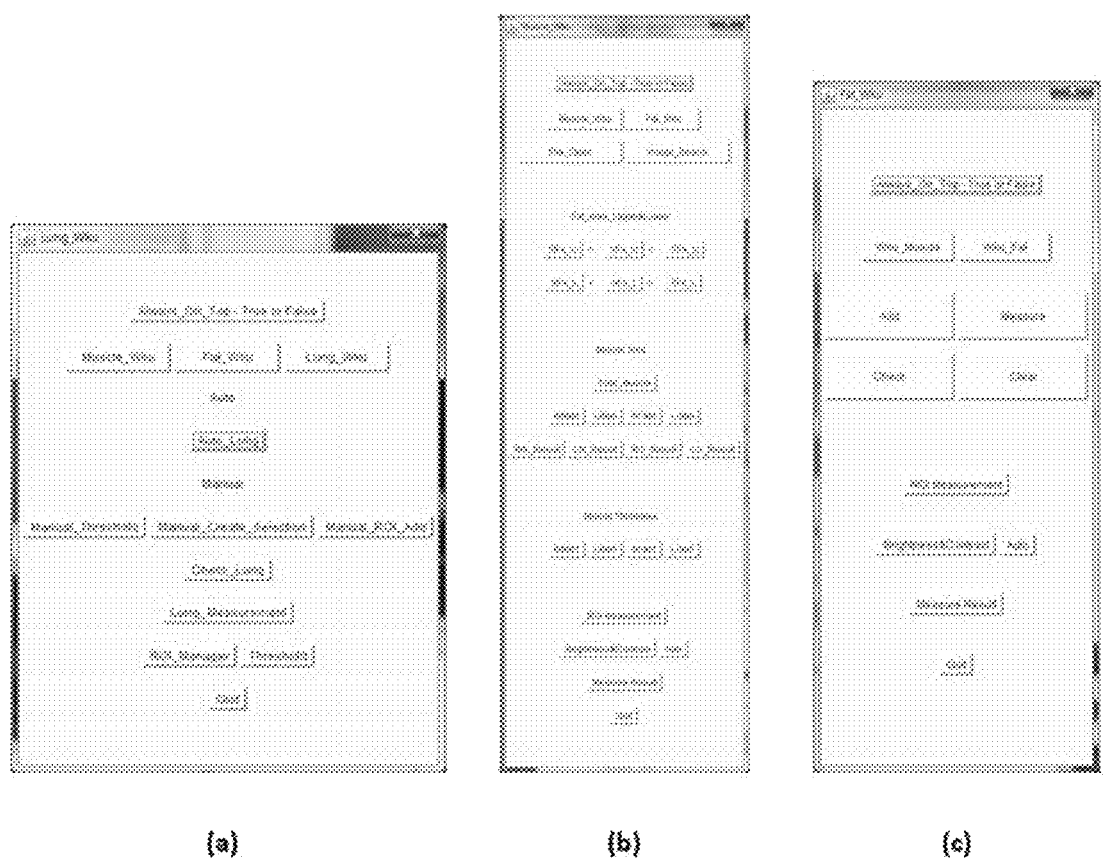
FIG. 6 is a diagram showing a GUIs provided through the image analysis method for multicenter study according to an embodiment of the present disclosure.

In particular, in the present disclosure, a graphic user interface (GUI) including various menus capable of selecting and adjusting information about an analysis target and an analysis method as in FIG. 6 is provided, so that not only the kind of analysis program but also the analysis program execution environment are adjusted according to the purpose and condition of the multicenter study, thereby constructing a more detailed and concrete analysis environment.

As a result, even though a multicenter study 1 and a multicenter study 2 have the same analysis program P1, the multicenter study 1 may activate only functions A and C of the analysis program P1, and the multicenter study 2 may activate all functions A, B, C and D of the analysis program P1. In this way, the analysis operation may be performed differently.

Then, each of the plurality of agency systems 200 determines whether or not to perform the analysis operation according to the research period. If it is determined to perform the analysis operation, patient images satisfying the research target selecting condition and the analyzing image selecting condition of the analysis guide are extracted from the patient medical treatment information stored in the patient database 220 managed by each of the plurality of agency systems 200. In addition, the extracted patient images are analyzed through the analysis program to acquire analysis data in a predetermined format, and the analysis data are provided to the multicenter study support system 100 (S5).

The analysis program of the present disclosure may include image processing algorithms such as a data preprocessing algorithm, an ROI (Region Of Interest) extraction algorithm, an analysis value measurement algorithm, an image conversion algorithm and a disease diagnosis algorithm, and the kind and usage of the analysis program may be variously changed depending on an analysis target and an analysis purpose.

Figure 7:
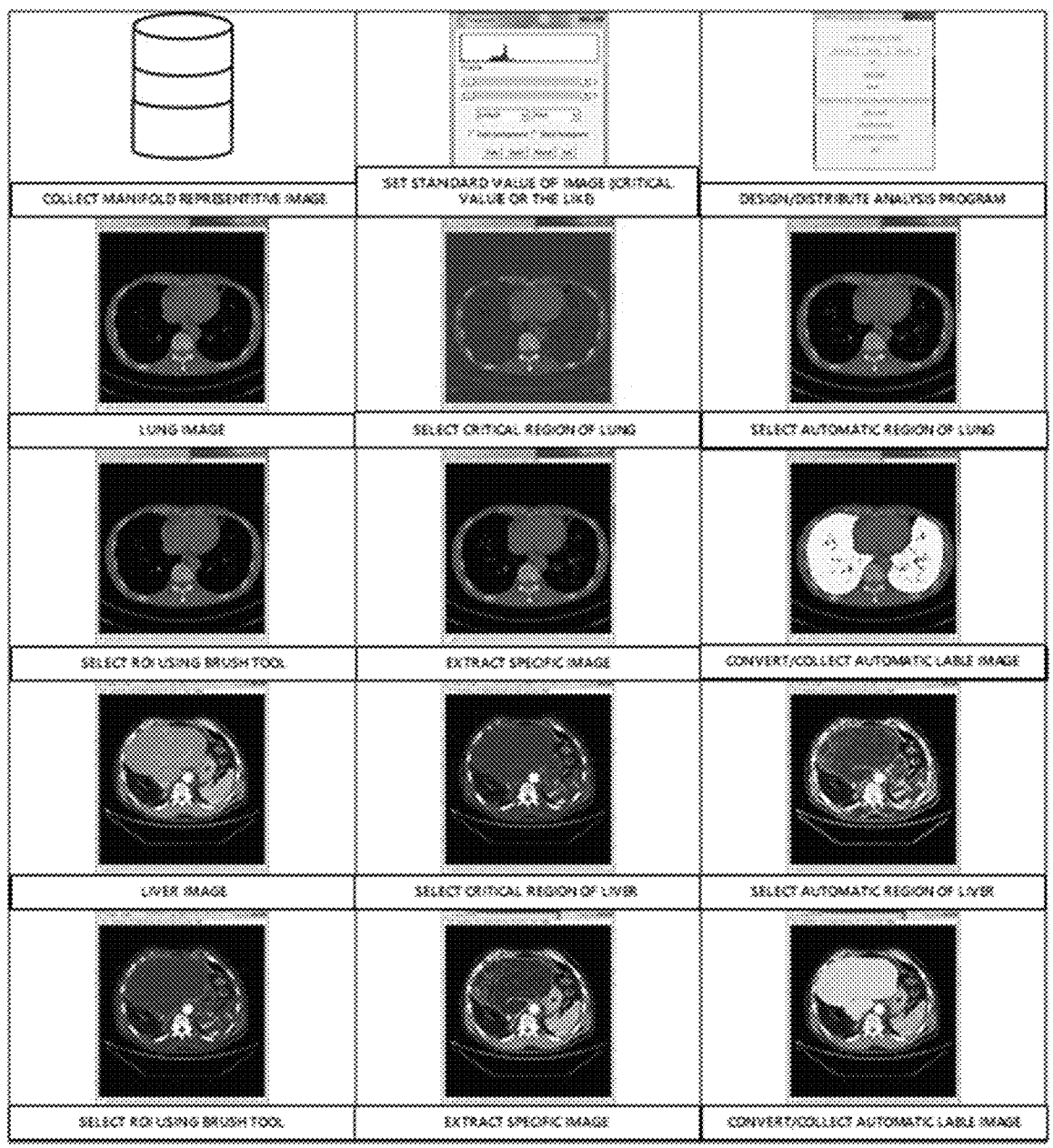
FIGS. 7 and 8 are diagrams for illustrating an analysis program according to an embodiment of the present disclosure.

Thus, in the present disclosure, as shown in (a) of FIG. 7, it is possible to perform a process of collecting patient images to be analyzed through the analysis program, a process of preprocessing data to set standard values of the images, a process of selecting one of the collected patient images as an analysis target image, a process of extracting an analysis object based on a critical region of the analysis target image or extracting an analysis object using a user tool (for example, a brush tool), a process of generating a masking image corresponding to the analysis object and then overlaying the masking image on the analysis target image to convert into and collect an automatic label image, a process of measuring an analysis value based on the image information of the analysis object, and a process of analyzing the images in the region of interest based on a preset diagnosis criterion and the analysis value to predict the degree of diseases and calculating and outputting disease diagnosis information. In addition, as shown in (b) of FIG. 7, analysis data is generated and provided as a result of the above processes. At this time, the analysis data may include at least one of the analysis value, the disease diagnosis information, the analysis object extraction image and the automatic label image.

Figure 8:
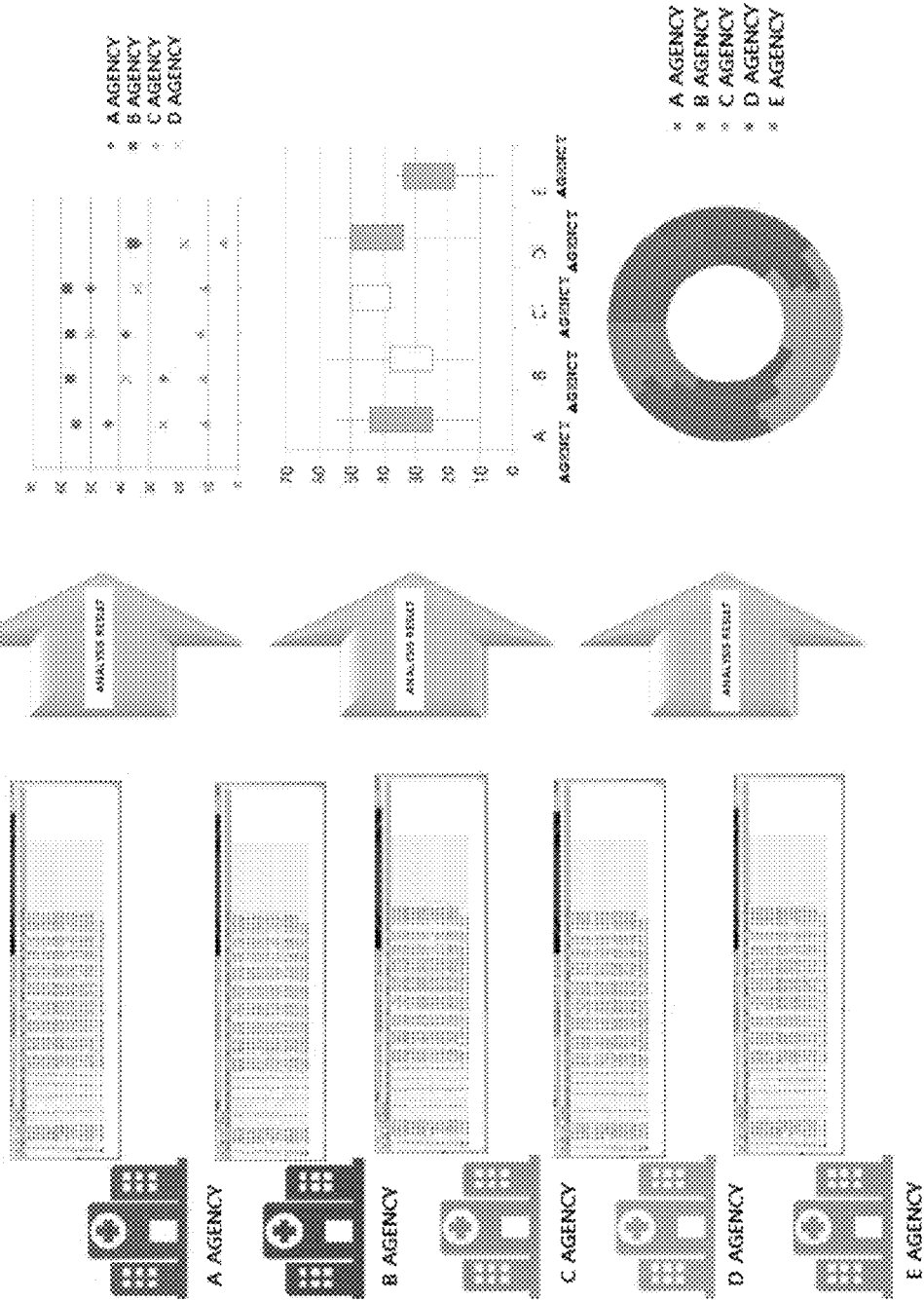

In addition, as in FIG. 8, it is also possible to generate and provide an integrated analysis result by integrating and analyzing the image analysis results of a plurality of manifold agencies.

The operation of acquiring and providing the analysis data by each of the plurality of agency systems 200 according to Step S5 is repeated until the multicenter study period is completed (S6).

In addition, the multicenter study support system 100 collects and stores all of the analysis data provided by the plurality of agency systems 200 (S7), and then statistically processes the analysis data according to a preset method and shares the statistical processing result with the plurality of agency systems 200 (S8).

The information shared in Step S8 may be at least one of the image analysis result, the original image and the statistical processing result, and the type of the shared information may be adjusted frequently by request of the agency system 200 or the like.

The analysis data collecting and processing operations of Steps S7 and S8 are also repeated until the multicenter study period is completed (S9).

The above description is merely illustrative of the technical idea of the present disclosure, and it will be understood by those skilled in the art that various changes and modifications may be made without departing from the essential characteristics of the present disclosure. Accordingly, the embodiments in the present disclosure are intended to illustrate the technical idea of the present disclosure without limiting the same, and the scope of the technical idea of the present disclosure is not limited by the embodiments. The scope of the present disclosure is to be construed in accordance with the appended claims, and all technical ideas within the scope equivalent thereto shall be construed as falling into the scope of the present disclosure.

What is claimed is:

1. A multicenter study support system, comprising:
a manifold recruiting unit configured to recruit and select of research agencies to perform multicenter study;
an analysis environment synchronizing unit configured to acquire an analysis guide and an analysis program corresponding to a purpose and condition of the multicenter study and distribute to each of the research agencies;
an analysis data collecting unit configured to collect and store analysis data acquired by each of the research agencies through the analysis guide and the analysis program; and
an analysis data processing unit configured to process the collected analysis data in a preset manner and share the data processing result with each of the research agencies,
wherein the analysis guide is information in which a data collection amount, a research period, a research target selecting condition, an analyzing image selecting condition, a research exclusion condition, a kind of an analysis program, an analysis program execution environment, and an analysis data uploading condition are predefined; and
the research agencies determine whether or not to perform the analysis program according to the research period, select a medical image to be analyzed according to the research target selecting condition and the analyzing image selecting condition, and analyze the selected medical image through the analysis program according to the analysis program execution environment to acquire the analysis data, and upload the analysis data to the analysis data collecting unit according to the analysis data uploading condition.

2. The multicenter study support system according to claim 1,
wherein the analysis program is a program for selecting and processing the medical image, then generating analysis data containing at least one of the selected medical image, the image processing result and an image conversion result, and uploading the analysis data to the multicenter study support system.

3. The multicenter study support system according to claim 2,
wherein the medical image is at least one of a CT (computerized tomography) image, a MRI (magnetic resonance imaging) image and an ultrasonic image, which is stored in the form of a DICOM (digital imaging and communication in medicine) file.

4. The multicenter study support system according to claim 3,
wherein the analysis program further has a function of anonymizing a DICOM header and patient information mapped with the medical image.

5. An agency system, comprising:
an analysis environment building unit configured to receive and install an analysis guide and an analysis program provided from a multicenter study support system and adjust a program execution period, an image selecting condition and an analysis program execution environment according to the analysis guide;
a patient database configured to store and manage medical treatment information of a plurality of patients and provide the medical treatment information to the analysis program; and
an analysis control unit configured to select at least one medical image by searching the patient database according to the image selecting condition, then analyze the medical image through the analysis program to obtain analysis data, and upload the analysis data to the multicenter study support system,
wherein the analysis guide is information in which a data collection amount, a research period, a research target selecting condition, an analyzing image selecting condition, a research exclusion condition, a kind of an analysis program, an analysis program execution environment, and an analysis data uploading condition are predefine;
the analysis control unit determine whether or not to perform the analysis program according to the research period, select the at least one medical image to be analyzed according to the research target selecting condition and the analyzing image selecting condition, and analyze the selected at least one medical image through the analysis program according to the analysis program execution environment to acquire the analysis data, and upload the analysis data to the multicenter study support system according to the analysis data uploading condition.

6. The agency system according to claim 5,
wherein the medical image is at least one of a CT image, an MRI image and an ultrasonic image, which is stored in the form of a DICOM file.

7. The agency system according to claim 6,
wherein the analysis control unit further has a function of anonymizing a DICOM header and patient information mapped with the medical image.

8. An image analysis method for multicenter study, comprising:
by a multicenter study support system, recruiting and selecting a plurality of agency systems to perform multicenter study, and then distributing an analysis guide and an analysis program corresponding to a purpose and condition of the multicenter study to each of the agency systems;
by each of the agency systems, collecting analysis data acquired through the analysis guide and the analysis program and then uploading the analysis data to the multicenter study support system; and
by the multicenter study support system, collecting and processing the uploaded analysis data, and then sharing the data processing result with each of the agency systems,
wherein the analysis guide is information in which a data collection amount, a research period, a research target selecting condition, an analyzing image selecting condition, a research exclusion condition, a kind of an analysis program, an analysis program execution environment, and an analysis data uploading condition are predefined;
each of the agency systems determine whether or not to perform the analysis program according to the research period, select a medical image to be analyzed according to the research target selecting condition and the analyzing image selecting condition, and analyze the selected medical image through the analysis program according to the analysis program execution environment to acquire the analysis data, and upload the analysis data to the multicenter study support system according to the analysis data uploading condition.

* * * * *